United States Patent
Sakaida

(10) Patent No.: US 7,171,031 B2
(45) Date of Patent: Jan. 30, 2007

(54) METHOD, APPARATUS, AND PROGRAM FOR RESTORING PHASE INFORMATION

(75) Inventor: Hideyuki Sakaida, Kaisei-machi (JP)

(73) Assignee: Fuji Photo Film Co., Ltd., Tokyo (JP)

( * ) Notice: Subject to any disclaimer, the term of this patent is extended or adjusted under 35 U.S.C. 154(b) by 817 days.

(21) Appl. No.: 10/418,082

(22) Filed: Apr. 18, 2003

(65) Prior Publication Data

US 2003/0202688 A1    Oct. 30, 2003

(30) Foreign Application Priority Data

Apr. 30, 2002 (JP) ............................. 2002-128662
Apr. 30, 2002 (JP) ............................. 2002-128663

(51) Int. Cl.
G06K 9/00 (2006.01)
G06K 9/40 (2006.01)
G06K 9/36 (2006.01)

(52) U.S. Cl. ...................... 382/128; 382/254; 382/276
(58) Field of Classification Search ............... 382/128, 382/132, 254, 272, 274, 276, 280; 128/9, 128/22; 378/62
See application file for complete search history.

(56) References Cited

U.S. PATENT DOCUMENTS 6,226,353 B1 *   5/2001   Wilkins et al. ............ 378/98.9
6,262,818 B1 *   7/2001   Cuche et al. .................. 359/9
6,493,422 B2 *   12/2002  Wilkins et al. ............ 378/98.9
6,594,335 B2 *   7/2003   Davidson ..................... 378/43

OTHER PUBLICATIONS

Allman, Brendan E., et al., Noninterometric Quantitative Phase Imaging With Soft X Rays, J. OPT. Soc. Am, vol. 17, N. 10, Oct. 2000. pp. 1732-1743.
Gureyev Timur E., et al, Hard X-Ray Quantitative Non-Interferometric Phase-Contrast Imaging, spie, vol. 3659, Feb. 1999, pp. 356-364.

* cited by examiner

Primary Examiner—Daniel Mariam
(74) Attorney, Agent, or Firm—Sughrue Mion, PLLC

(57) ABSTRACT

A method of restoring phase information using a phase-contrast method, which can improve estimated accuracy of a phase. This method is a method of restoring phase information by detecting intensity of radiation, and includes the steps of: (a) obtaining three first differential signals representing differentials between one image signal and another image signal based on four image signals obtained by detecting intensity of radiation on four planes and representing radiation image information respectively; (b) obtaining second and third differential signals representing differentials between image signals relative to two directions orthogonal to each other within the planes with respect to the three image signals; (c) obtaining a Laplacian of phase based on the three image signals and three sets of the first to third differential signals; and (d) performing inverse Laplacian operation on the Laplacian of phase so as to restore phase information.

10 Claims, 11 Drawing Sheets

METHOD, APPARATUS, AND PROGRAM FOR RESTORING PHASE INFORMATION

BACKGROUND OF THE INVENTION

1. Field of the Invention

The present invention relates to a method, an apparatus, and a program for restoring phase information used for constructing an image based on image information obtained by radiation imaging etc. Note that, in this application, the term "radiation" indicates radiation in a broad sense including a corpuscular beam such as an electron beam, and an electromagnetic wave, in addition to common radiation such as an X-ray, an α-ray, a β-ray, a γ-ray, and ultraviolet rays.

2. Description of a Related Art

Conventionally, an imaging method using an X-ray etc. is utilized in various fields, and particularly, in the medical field, the method is one of the most important means for diagnosis. Since the first X-ray photograph was implemented, the X-ray photography method has been repeatedly improved, and a method using a combination of a fluorescent screen and an X-ray film is in the mainstream at present. On the other hand, in recent years, various digitized devices applying X-ray CT, ultrasonic waves, MRI, etc. are in practical use, and construction of a diagnostic information processing system etc. in hospitals is being promoted. Many studies are also made for digitizing the imaging system with regard to X-ray images. Digitizing the imaging system enables to store a large amount of data for a long period without degradation in image, and helps to make progress toward the medical diagnostic information processing system.

Now, a radiation image obtained as described above is generated by converting intensity of the radiation transmitted through an object into brightness of the image. For example, when performing imaging on a region including a bone part, the radiation transmitted through the bone part is largely attenuated, and the radiation transmitted through a region other than the bone part, i.e., a soft part is slightly attenuated. In this case, since the difference in intensity between the radiation transmitted through different tissues is large, a high-contrast radiation image can be obtained.

On the other hand, for example, when imaging a region of the soft part such as a breast, since radiation is easily transmitted through the soft part as a whole, the difference between tissues in the soft part is difficult to appear as the difference in intensity of the transmitted radiation. Therefore, only a low-contrast image can be obtained with respect to the soft part. Thus, the radiation imaging method is not suitable as a method of visualizing the slight difference between tissues in the soft part.

Here, as information included in the radiation transmitted through the object, there is phase information in addition to intensity information. Recently, a phase-contrast method of generating an image using this phase information is under study. The phase-contrast method is a phase information restoration technology to convert phase difference produced by an X-ray etc. transmitted through the object into brightness of an image.

The phase-contrast method includes techniques for obtaining phase difference based on interference X-rays produced by using an interferometer or a zone plate, and for obtaining phase difference based on diffracted X-rays. Of these techniques, the diffraction technique for obtaining phase difference based on diffracted X-rays is to obtain phase difference according to the following principle. An X-ray, for example, propagates within a material since a wave progresses similarly to light. The propagation velocity thereof varies in accordance with the refractive index the material has. Therefore, when irradiating an object with an X-ray that has a uniform phase, the way the X-ray propagates varies in accordance with the difference between tissues in the object. Thereby, the wavefront of the X-ray transmitted through the object is distorted and, as a result, diffraction fringes are produced on the X-ray image obtained based on the transmitted X-ray. The pattern of the diffraction fringes differs in accordance with the distance between the screen on which the X-ray image is formed and the object, and the wavelength of the X-ray. Thus, analyzing two or more X-ray images having different patterns of diffraction fringes, phase differences of the X-ray produced on the respective positions on the screen can be obtained. Converting the phase differences into brightness, an X-ray image that clearly shows the difference between tissues in the object can be obtained.

Particularly, in the radiation after transmitted through a soft part of the object, since the difference in phase is larger than the difference in intensity in accordance with the difference between tissues through which the radiation has been transmitted, the subtle difference between tissues can be visualized by using the phase-contrast method.

In order to use the above phase-contrast method, imaging conditions in radiation imaging or techniques for restoring phase from patterns of diffraction fringes are under study.

For example, B. E. Allman et al. "Noninterferometric quantitative phase imaging with soft x rays", J. Optical Society of America A, Vol. 17, No. 10 (October 2000), pp. 1732–1743, discloses that an X-ray image is constructed by performing phase restoration based on image information obtained by imaging with soft X-rays.

In this reference, the basic expression of phase restoration, TIE (transport of intensity equation) is used.

$$\kappa \frac{\partial I(\vec{r})}{\partial z} = -\nabla_\perp \cdot \{I(\vec{r})\nabla_\perp \phi(\vec{r})\} \quad (1)$$

Where $$\nabla_\perp = \left(\frac{\partial}{\partial x}, \frac{\partial}{\partial y}\right)$$

In addition, κ denotes wave number.

Here, a principle of the phase restoration will be described by referring to FIG. 11. As shown in FIG. 11, an X-ray having a wavelength λ is output from the left side of the drawing, transmitted through an object plane 101 and enters a screen 102 at a distance of z from the object plane 101. Assuming that the intensity and the phase of the X-ray at a position (x,y) on the screen 102 are I(x,y) and φ(x,y), respectively, a relationship between intensity I(x,y) and phase φ(x,y) is expressed by the following expression. Here, the intensity I is square of amplitude of wave.

$$\frac{2\pi}{\lambda}\frac{\partial I(x,y)}{\partial z} = -\nabla \cdot \{I(x,y)\nabla \phi(x,y)\} \quad (2)$$

Substituting $\kappa=2\pi/\lambda$ into expression (2) and rewriting (x,y) components into vector r, TIE expressed by expression (1) is derived.

However, since the above TIE is difficult to be solved, TIE has been used mainly by performing approximation thereon. For example, T. E. Gureyev et al. "Hard X-ray quantitative non-interferometric phase-contrast imaging", SPIE Vol. 3659 (1999), pp. 356–364, discloses that an X-ray image is constructed by performing phase restoration based on image information obtained by imaging with hard X-rays.

In this reference, TIE expressed by expression (1) is approximated as follows. First, expression (1) is developed. Note that, in the following expressions, the vector r in the above reference is rewritten into (x,y) components.

$$-\kappa\frac{\partial I(x,y)}{\partial z} = \left(\frac{\partial}{\partial x}, \frac{\partial}{\partial y}\right) \cdot \left(I(x,y)\frac{\partial \phi(x,y)}{\partial x}, I(x,y)\frac{\partial \phi(x,y)}{\partial y}\right) = \qquad (3)$$

$$\frac{\partial}{\partial x}\left(I(x,y)\frac{\partial \phi(x,y)}{\partial x}\right) + \frac{\partial}{\partial y}\left(I(x,y)\frac{\partial \phi(x,y)}{\partial y}\right) =$$

$$I(x,y)\left(\frac{\partial^2 \phi(x,y)}{\partial x^2} + \frac{\partial^2 \phi(x,y)}{\partial y^2}\right) +$$

$$\frac{\partial I(x,y)}{\partial x}\frac{\partial \phi(x,y)}{\partial x} + \frac{\partial I(x,y)}{\partial y}\frac{\partial \phi(x,y)}{\partial y} =$$

$$I(x,y)\nabla^2 \phi(x,y) + \nabla I(x,y) \cdot \nabla \phi(x,y)$$

Where $$\nabla^2 = \frac{\partial^2}{\partial x^2} + \frac{\partial^2}{\partial y^2}$$

Approximating the second term on the right side of expression (3) to zero, the approximation expression expressed by the following expression (4) is obtained.

$$\frac{\partial I(x,y)}{\partial z} \cong -\frac{I(x,y)}{\kappa}\nabla^2 \phi(x,y) \qquad (4)$$

In expression (4), $\phi(x,y)$ can be obtained from $I(x,y)$ by a solution method such as the finite element method.

However, in the approximation expression (4), there is a problem that the estimated accuracy of the phase $\phi(x,y)$ becomes low when the approximation on the second term $\nabla I(x,y) \cdot \nabla \phi(x,y)$ included in expression (3) to zero is not appropriate.

Further, using a differential coefficient of intensity obtained from two pieces of detection data instead of the left side of expression (4), a phase can be restored by using at least two images. However, there is a problem that, when the phase is restored from a small number of images as many as two, the estimated accuracy of the phase becomes low in the case where the images are degraded due to noise etc.

SUMMARY OF THE INVENTION

The present invention has been achieved in view of the above-described problems. An object of the present invention is to provide a phase information restoring method that enables to improve estimated accuracy of a phase when constructing a radiation image by the phase-contrast method. Another object of the present invention is to provide a phase information restoring apparatus and a phase information restoring program for implementing the above phase information restoring method.

In order to solve the above-described problems, a phase information restoring method according to a first aspect of the present invention is a method of restoring phase information of radiation transmitted through an object on the basis of an image signal obtained by detecting intensity of the radiation transmitted through the object, the method comprises the steps of: (a) obtaining at least three first differential signals representing differentials between one image signal and another image signal on the basis of at least four image signals obtained by detecting intensity of radiation on at least four planes that are parallel and positioned at different distances from the object, the at least four image signals respectively representing radiation image information on the at least four planes; (b) obtaining second differential signals and third differential signals representing differentials between image signals relative to two directions orthogonal to each other within the planes with respect to at least three image signals; (c) obtaining a Laplacian of phase on the basis of the at least three image signals and at least three sets of the first to third differential signals; and (d) performing inverse Laplacian operation on the Laplacian of phase so as to restore phase information.

A phase information restoring apparatus according to the first aspect of the present invention is an apparatus for restoring phase information of radiation transmitted through an object on the basis of an image signal obtained by detecting intensity of the radiation transmitted through the object, the apparatus comprises: differential processing means for obtaining at least three first differential signals representing differentials between one image signal and another image signal on the basis of at least four image signals obtained by detecting intensity of radiation on at least four planes that are parallel and positioned at different distances from the object, the at least four image signals respectively representing radiation image information on the at least four planes, and second differential signals and third differential signals representing differentials between image signals relative to two directions orthogonal to each other within the planes with respect to at least three image signals; Laplacian processing means for obtaining a Laplacian of phase on the basis of the at least three image signals and at least three sets of the first to third differential signals; inverse Laplacian processing means for performing inverse Laplacian operation on the Laplacian of phase so as to restore phase information.

A phase information restoring program according to the first aspect of the present invention is a program used for restoring phase information of radiation transmitted through an object on the basis of an image signal obtained by detecting intensity of the radiation transmitted through the object, the program allows a CPU to execute the procedures of: obtaining at least three first differential signals representing differentials between one image signal and another image signal on the basis of at least four image signals obtained by detecting intensity of radiation on at least four planes that are parallel and positioned at different distances from the object, the at least four image signals respectively representing radiation image information on the at least four planes; obtaining second differential signals and third differential signals representing differentials between image signals relative to two directions orthogonal to each other within the planes with respect to at least three image signals; obtaining a Laplacian of phase on the basis of the at least three image signals and at least three sets of the first to third differential signals; and performing inverse Laplacian operation on the Laplacian of phase so as to restore phase information.

According to the first aspect of the present invention, since approximation is not performed except on a differential coefficient part of intensity when using the expression of phase restoration, high-accuracy phase restoration can be achieved.

A phase information restoring method according to a second aspect of the present invention is a method of restoring phase information of radiation transmitted through an object on the basis of an image signal obtained by detecting intensity of the radiation transmitted through the object, the method comprises the steps of: (a) obtaining plural differential signals representing differentials between one image signal and another image signal on the basis of at least three image signals obtained by detecting intensity of radiation on at least three planes that are positioned at different distances from the object, the at least three image signals respectively representing radiation image information on the at least three planes; (b) respectively obtaining Laplacian of phases on the basis of the plural differential signals and one of the at least three image signals; (c) performing inverse Laplacian operation on the Laplacian of phases so as to obtain plural phases respectively; (d) calculating an average value of the plural phases obtained at step (c).

A phase information restoring apparatus according to the second aspect of the present invention is an apparatus for restoring phase information of radiation transmitted through an object on the basis of an image signal obtained by detecting intensity of the radiation transmitted through the object, the apparatus comprises: differential processing means for obtaining plural differential signals representing differentials between one image signal and another image signal on the basis of at least three image signals obtained by detecting intensity of radiation on at least three planes that are positioned at different distances from the object, the at least three image signals respectively representing radiation image information on the at least three planes; Laplacian processing means for respectively obtaining Laplacian of phases on the basis of the plural differential signals and one of the at least three image signals; inverse Laplacian processing means for performing inverse Laplacian operation on the Laplacian of phases so as to obtain plural phases respectively; average processing means for calculating an average value of the plural phases obtained in the inverse Laplacian processing means.

A phase information restoring program according to the second aspect of the present invention is a program used for restoring phase information of radiation transmitted through an object on the basis of an image signal obtained by detecting intensity of the radiation transmitted through the object, the program allows a CPU to execute the procedures of: (a) obtaining plural differential signals representing differentials between one image signal and another image signal on the basis of at least three image signals obtained by detecting intensity of radiation on at least three planes that are positioned at different distances from the object, the at least three image signals respectively representing radiation image information on the at least three planes; (b) respectively obtaining Laplacian of phases on the basis of the plural differential signals and one of the at least three image signals; (c) performing inverse Laplacian operation on the Laplacian of phases so as to obtain plural phases respectively; (d) calculating an average value of the plural phases obtained in procedure (c).

According to the second aspect of the present invention, high-accuracy phase restoration can be achieved by restoring plural phases and averaging the restored plural phases.

DESCRIPTION OF THE PREFERRED EMBODIMENTS

Figure 1:
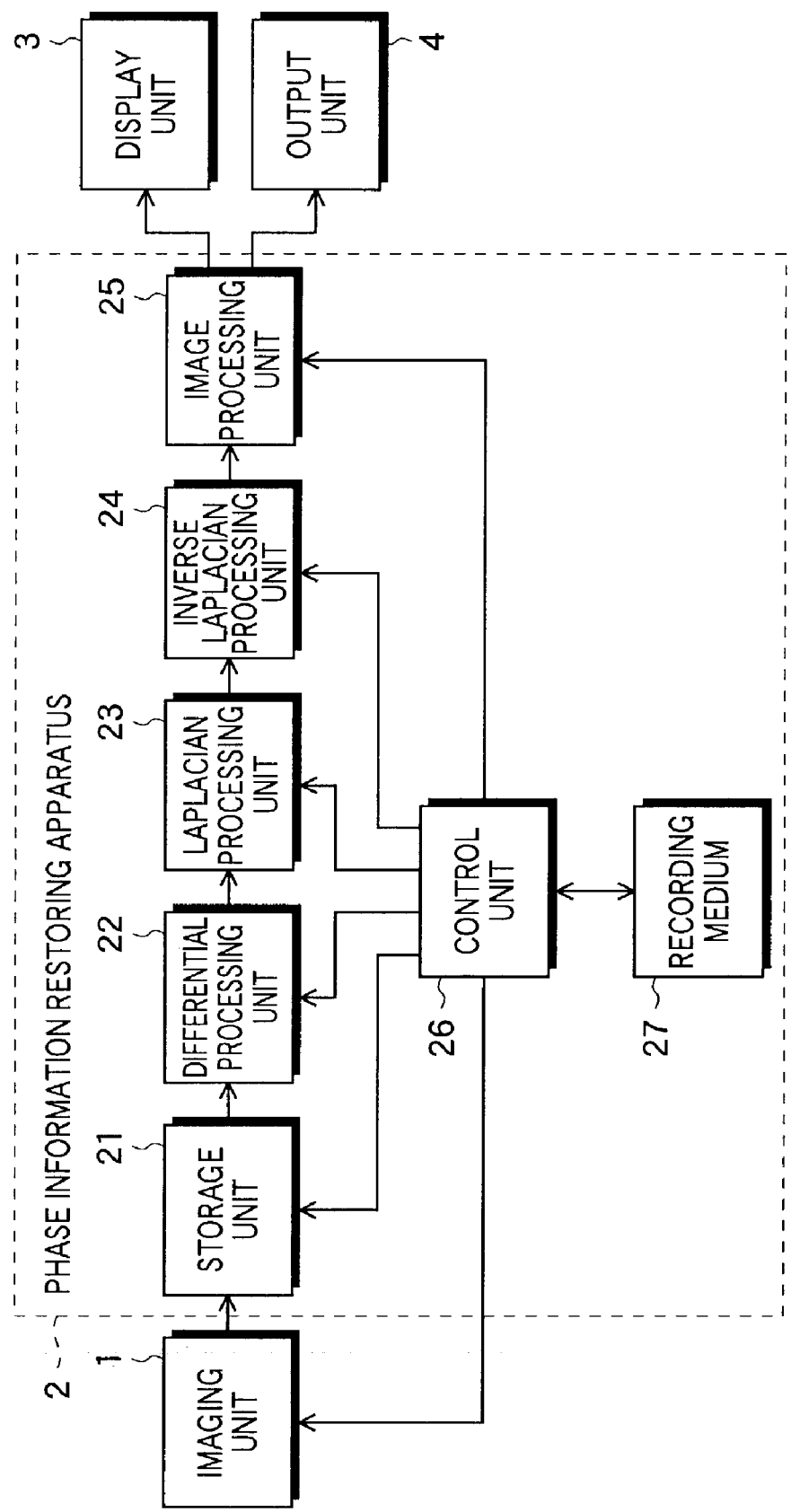
FIG. 1 is a block diagram showing an X-ray imaging system including a phase information restoring apparatus according to a first embodiment of the present invention.

Now, referring to the drawings, embodiments of the present invention will be described in detail. The same component elements will be given with the same reference numerals and the descriptions thereof will be omitted.

FIG. 1 is a block diagram showing an X-ray imaging system including a phase information restoring apparatus according to a first embodiment of the present invention. This X-ray imaging system has an imaging unit 1 for irradiating the object with an X-ray so as to output detection data that represents image information of an object, a phase information restoring apparatus 2 for generating image data based on the detection data, a display unit 3 for displaying a visible image based on the image data, and an output unit 4 for printing out the visible image on a film etc.

Figure 2:
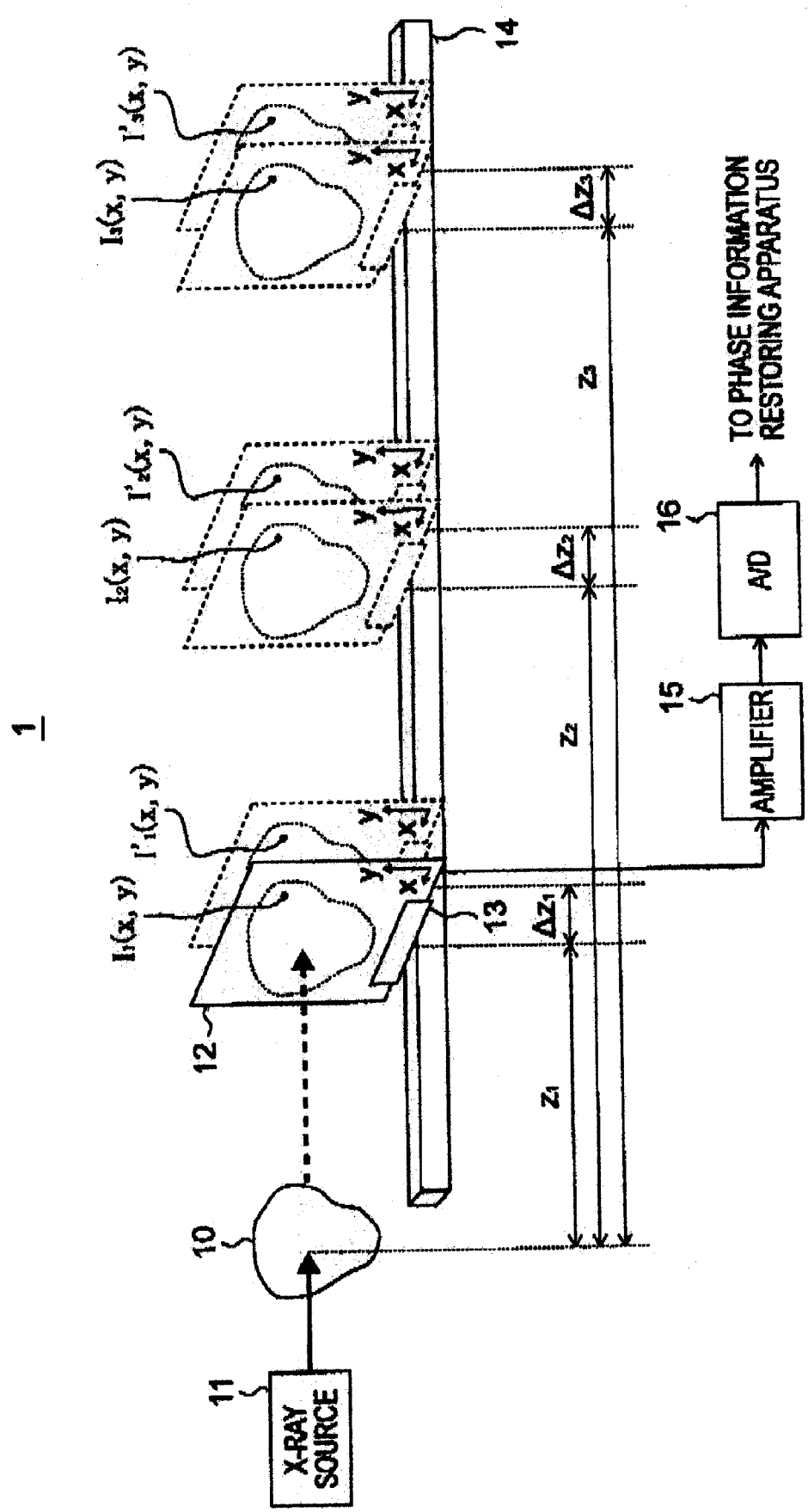
FIG. 2 is a diagram showing a structure of an imaging unit shown in FIG. 1.

FIG. 2 is a diagram showing a structure of the imaging unit 1. As a X-ray source 11, it is desirable to use a X-ray source generating a radiation beam that is highly coherent and monochromatic. Here, the highly monochromatic beam indicates a beam that mainly has a single wavelength. For this purpose, in the embodiment, a synchrotron radiation source that generates X-rays is used as the X-ray source 11. The synchrotron radiation is an electromagnetic wave that is generated by accelerating an electron or bending a traveling direction of an electron. The X-ray generated from the X-ray source 11 is transmitted through an object 10 and enters a sensor 12.

The sensor 12 detects the incident X-ray. As the sensor 12, a two-dimensional sensor such as a CCD (charge coupled device) having a plurality of detecting elements that convert intensity of the applied X-ray into electric signals and output the signals is used. The detection signal output from the sensor 12 is amplified by an amplifier 15, converted into a digital signal (detection data) by an A/D converter 16, and output to the phase information restoring apparatus 2.

The sensor 12 is held by a holding portion 13. The holding portion 13 is movably supported on a rail 14. The position of the holding portion 13 is controlled by a control unit, which will be described later, of the phase information restoring apparatus 2, and a distance between the object 10 and the sensor 12 is changed under the control of the control unit. Note that the distance between the object 10 and the sensor 12 is referred to as an imaging distance hereinafter.

Referring to FIG. 1 again, the phase information restoring apparatus 2 has a storage unit 21 for temporarily storing the detection data output from the imaging unit 1, a differential processing unit 22 for obtaining a differential coefficient between detection data at different imaging distances and a differential coefficient between detection data at the same imaging distance, a Laplacian processing unit 23 for calculating a value that corresponds to a Laplacian of phase, an inverse Laplacian processing unit 24 for performing inverse Laplacian operation for phase restoration, an image processing unit 25 for generating image data on the basis of the restored phase information, and a control unit 26 for controlling the respective units 21–25 and the imaging distance in the imaging unit 1. The phase information restoring apparatus 2 may be configured with a digital circuit or software and a CPU. With a CPU, the control unit 26 including the CPU processes the detection data on the basis of a phase information restoring program recorded on a recording medium 27. As the recording medium 27, a flexible disk, a hard disk, an MO, an MT, a RAM, a CD-ROM, a DVD-ROM, etc. are applicable.

The display unit 3 is a display device such as a CRT, and displays a visible image based on image data that represents the phase information restored by the phase information restoring apparatus 2. The output unit 4 is a laser printer, for example, and prints out the visible image on a film etc. on the basis of the image data.

Next, a principle of a phase information restoring method according to the present invention will be described. The phase information restoring method according to the present invention is a method of constructing a visible image by the phase-contrast method, and the phase restoration is performed on the basis of plural diffraction fringe images obtained with respect to an object by using the basic expression of phase restoration, TIE (transport of intensity equation).

TIE expressed by the following expression (5) is transformed so as to obtain expression (6).

$$-\kappa \frac{\partial I(x,y)}{\partial z} = \nabla \cdot \{I(x,y)\nabla \phi(x,y)\} \quad (5)$$

$$-\kappa \frac{\partial I(x,y)}{\partial z} = I(x,y)\nabla^2 \phi(x,y) + \nabla I(x,y) \cdot \nabla \phi(x,y) = \quad (6)$$

$$I(x,y)\nabla^2 \phi(x,y) + \frac{\partial I(x,y)}{\partial x}\frac{\partial \phi(x,y)}{\partial x} + \frac{\partial I(x,y)}{\partial y}\frac{\partial \phi(x,y)}{\partial y}$$

Where $I(x,y)$ is detection data representing intensity of diffracted X-ray at a position $(x,y)$ on a plane at a distance of z from the object.

In expression (6), the Laplacian $\nabla^2 \phi(x,y)$ and the gradients $(\partial \phi(x,y)/\partial x, \partial \phi(x,y)/\partial y)$ of the phase $\phi(x,y)$ to be obtained are unknown. If at least three gradients $\nabla I=(\partial I/\partial x, \partial I/\partial y, \partial I/\partial z)$ of the intensity of the diffracted X-ray can be obtained, expression (6) can be solved.

Substituting elements of the gradients $\nabla I_1$ to $\nabla I_3$ of the intensity of the diffracted X-ray into expression (6), it is expressed with matrices by expression (7).

$$-\kappa \begin{pmatrix} \frac{\partial I_1(x,y)}{\partial z} \\ \frac{\partial I_2(x,y)}{\partial z} \\ \frac{\partial I_3(x,y)}{\partial z} \end{pmatrix} = \begin{pmatrix} I_1(x,y) & \frac{\partial I_1(x,y)}{\partial x} & \frac{\partial I_1(x,y)}{\partial y} \\ I_2(x,y) & \frac{\partial I_2(x,y)}{\partial x} & \frac{\partial I_2(x,y)}{\partial y} \\ I_3(x,y) & \frac{\partial I_3(x,y)}{\partial x} & \frac{\partial I_3(x,y)}{\partial y} \end{pmatrix} \begin{pmatrix} \nabla^2 \phi(x,y) \\ \frac{\partial \phi(x,y)}{\partial x} \\ \frac{\partial \phi(x,y)}{\partial y} \end{pmatrix} \quad (7)$$

Expression (7) can be solved using an inverse matrix, for example.

As described above, in the embodiment, approximation in TIE is minimized to raise the accuracy of the phase restoration and the operation is simplified by using a matrix form.

Figure 3:
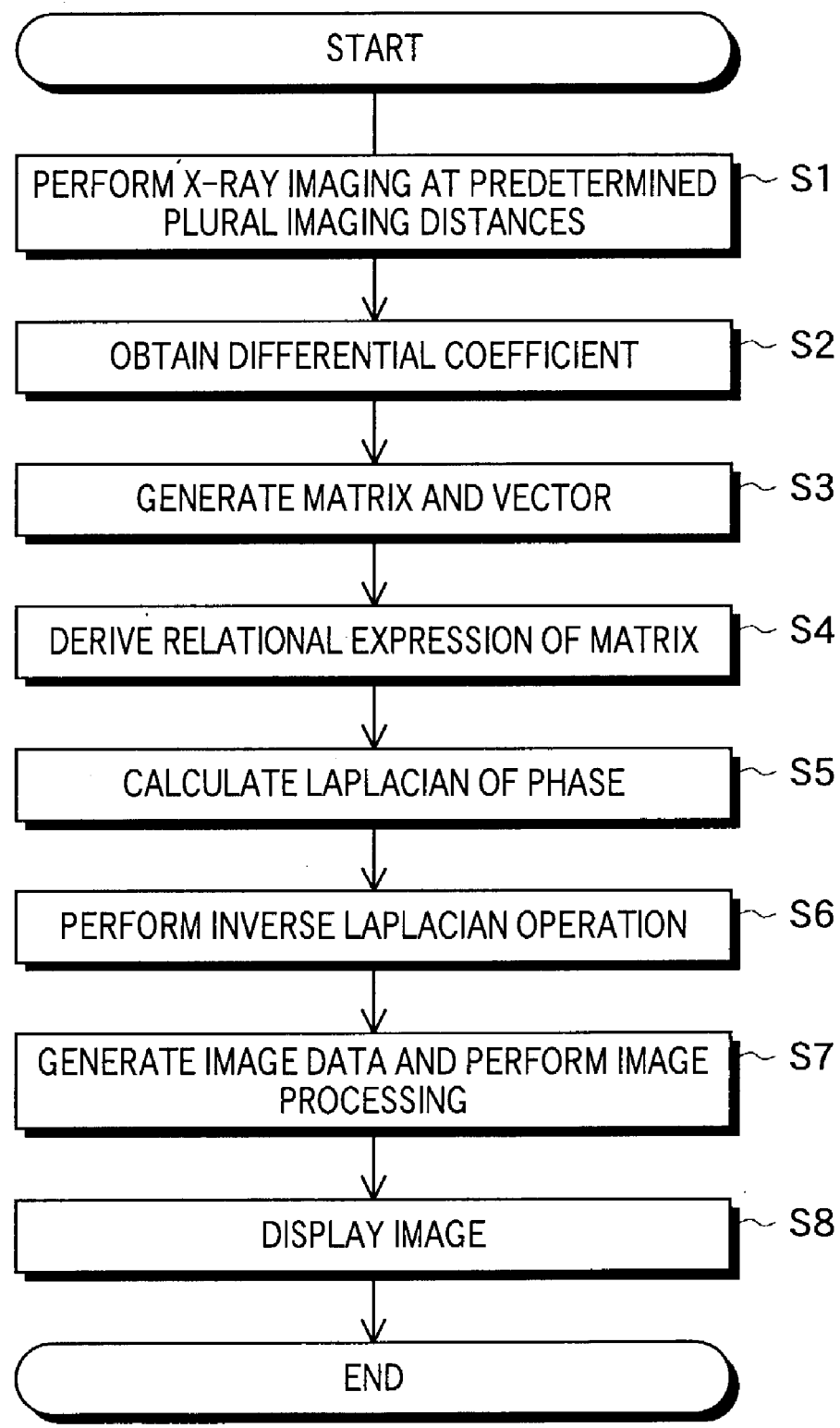
FIG. 3 is a flowchart showing a phase information restoring method according to the first embodiment of the present invention.

Next, referring to FIGS. 1–3, the phase information restoring method according to the first embodiment of the present invention will be described. FIG. 3 is a flowchart showing the phase information restoring method according to the first embodiment of the present invention. In the embodiment, a visible image is constructed by using detection data representing six diffraction fringe images taken while changing the imaging distance as shown in FIG. 2.

First, at step S1, X-ray imaging is performed. The sensor 12 is positioned at the position where the imaging distance is $z_1$ as shown in FIG. 2 and irradiating the object 10 with an X-ray so as to perform the X-ray imaging. Then, the sensor 12 moved to the position where the imaging distance is $(z_1+\Delta z_1)$ and the X-ray imaging is performed. Similarly, the X-ray imaging is repeated with the sensor positioned at the imaging distances of $z_2$, $(z_2+\Delta z_2)$, $z_3$, and $(z_3+\Delta z_3)$. Thereby, the detection data representing diffraction fringe images are obtained.

By the X-ray imaging at step S1, detection data $I_1(x,y)$, $I_1'(x,y)$, $I_2(x,y)$, $I_2'(x,y)$, $I_3(x,y)$, and $I_3'(x,y)$ are sequentially input to the phase information restoring apparatus 2. Here, the detection data $I_1(x,y)$ represents intensity of the diffracted X-ray at the position $(x,y)$ on a plane at the imaging distance of $z_1$. Similarly, the detection data $I_1'(x,y)$, $I_2(x,y)$, $I_2'(x,y)$, $I_3(x,y)$, and $I_3'(x,y)$ represent intensity of the diffracted X-ray at the positions $(x,y)$ on planes at the imaging distances of $(z_1+\Delta z_1)$, $z_2$, $(z_2+\Delta z_2)$, $z_3$, and $(z_3+\Delta z_3)$, respectively. The detection data sequentially stored in the storage unit 21 of the phase information restoring apparatus 2.

Next, at steps S2–S6, the phase information restoring apparatus 2 restores a phase on the basis of the detection data stored in the storage unit 21.

First, at step S2, the differential processing unit 22 obtains a differential coefficient between detection data $I_N$ and detection data $I_N'$ using the following expression (8), where $\Delta z_N = z_N' - z_N$ and N=1, 2, and 3.

$$\frac{\partial I_N(x,y)}{\partial z} = \frac{I_N'(x,y) - I_N(x,y)}{\Delta z_N} \quad (8)$$

Then, at step S3, the Laplacian processing unit 23 obtains the gradients $\partial I(x,y)/\partial x$ and $\partial I(x,y)/\partial y$ of the detection data at respective positions (x,y) on xy plane, and generates matrix A(x,y) with three rows and three columns as expressed by expression (9).

$$A(x,y) = \begin{pmatrix} I_1(x,y) & \frac{\partial I_1(x,y)}{\partial x} & \frac{\partial I_1(x,y)}{\partial y} \\ I_2(x,y) & \frac{\partial I_2(x,y)}{\partial x} & \frac{\partial I_2(x,y)}{\partial y} \\ I_3(x,y) & \frac{\partial I_3(x,y)}{\partial x} & \frac{\partial I_3(x,y)}{\partial y} \end{pmatrix} \quad (9)$$

Further, the Laplacian processing unit 23 generates vector D(x,y) expressed by expression (10) on the basis of the differential coefficient obtained by expression (8).

$$\overrightarrow{D(x,y)} = \begin{pmatrix} \frac{\partial I_1(x,y)}{\partial z} \\ \frac{\partial I_2(x,y)}{\partial z} \\ \frac{\partial I_3(x,y)}{\partial z} \end{pmatrix} \quad (10)$$

Next, at step S4, the Laplacian processing unit 23 derives the relational expression of matrix (11) using the matrix A(x,y) and the vector D (x,y) obtained by expressions (9) and (10).

$$-\kappa \begin{pmatrix} \frac{\partial I_1(x,y)}{\partial z} \\ \frac{\partial I_2(x,y)}{\partial z} \\ \frac{\partial I_3(x,y)}{\partial z} \end{pmatrix} = \begin{pmatrix} I_1(x,y) & \frac{\partial I_1(x,y)}{\partial x} & \frac{\partial I_1(x,y)}{\partial y} \\ I_2(x,y) & \frac{\partial I_2(x,y)}{\partial x} & \frac{\partial I_2(x,y)}{\partial y} \\ I_3(x,y) & \frac{\partial I_3(x,y)}{\partial x} & \frac{\partial I_3(x,y)}{\partial y} \end{pmatrix} \begin{pmatrix} \nabla^2 \phi(x,y) \\ \frac{\partial \phi(x,y)}{\partial x} \\ \frac{\partial \phi(x,y)}{\partial y} \end{pmatrix} \quad (11)$$

Further, at step S5, the Laplacian processing unit 23 multiplies both sides of expression (11) by an inverse matrix of the matrix A(x,y) from the left side as expressed by expression (12) so as to obtain vector $\Phi(x,y)$.

$$\overrightarrow{\Phi(x,y)} = -\kappa \begin{pmatrix} I_1(x,y) & \frac{\partial I_1(x,y)}{\partial x} & \frac{\partial I_1(x,y)}{\partial y} \\ I_2(x,y) & \frac{\partial I_2(x,y)}{\partial x} & \frac{\partial I_2(x,y)}{\partial y} \\ I_3(x,y) & \frac{\partial I_3(x,y)}{\partial x} & \frac{\partial I_3(x,y)}{\partial y} \end{pmatrix}^{-1} \begin{pmatrix} \frac{\partial I_1(x,y)}{\partial z} \\ \frac{\partial I_2(x,y)}{\partial z} \\ \frac{\partial I_3(x,y)}{\partial z} \end{pmatrix} = \quad (12)$$

$$\begin{pmatrix} \nabla^2 \phi(x,z) \\ \frac{\partial \phi(x,y)}{\partial x} \\ \frac{\partial \phi(x,y)}{\partial y} \end{pmatrix}$$

The first element of the vector $\Phi(x,y)$ corresponds to the Laplacian $\nabla^2 \phi(x,y)$ of the phase.

Then, at step S6, the inverse Laplacian processing unit 24 performs inverse Laplacian operation on the Laplacian $f(x,y) = \nabla^2 \phi(x,y)$ obtained at step S5 so as to obtain phase $\phi(x,y)$.

Here, the inverse Laplacian operation will be described in detail. A Fourier transform of f(x,y) is expressed by the following expression (13).

$$F[f(x,y)] = F[\nabla^2 \phi(x,y)] = -4\pi^2(u^2+v^2)F[\phi(x,y)] \quad (13)$$

Where u and v are spatial frequencies that correspond to x and y.

Hereby, the phase $\phi(x,y)$ is expressed as expression (14).

$$\phi(x,y) = F^{-1}\left[-\frac{1}{4\pi^2(u^2+v^2)}F[f(x,y)]\right] \quad (14)$$

Using expression (14), the inverse Laplacian operation can be performed. That is, the restored phase $\phi(x,y)$ can be obtained by performing the Fourier transform of f(x,y), multiplying by $\{-4\pi^2(u^2+v^2)\}^{-1}$ and then performing an inverse Fourier transform thereon.

Here, a value of $\{-4^2(u^2+v^2)\}^{-1}$ may be calculated in advance within the range where |u| and |v| are not more than a predetermined value, and used when the operation expressed by expression (14) is performed. That is, in the case where the predetermined value "const" is set, for |u|, |v|≦const, the value of the following expression is used in expression (14).

$\{-4\pi^2(u^2+v^2)\}^{-1}$=(the value calculated in advance) For |u|, |v|>const, the value of the following expression is used in expression (14).

$-4\pi^2(u^2+v^2)\}^{-1}=0$

Thereby, the inverse Laplacian operation can be performed at high speed.

Next, at step S7, the image processing unit 25 generates image data on the basis of the restored phase $\phi(x,y)$. That is, the image processing unit 25 converts the phase $\phi(x,y)$ in each pixel into data representing brightness, and performs necessary image processing such as gradation processing and interpolation processing, etc.

At step S8, the display unit 3 and the output unit 4 display a visible image on a screen, a film, etc. on the basis of the image data generated as described above.

Although, in the embodiment, the method of restoring phase by using three differential coefficients obtained from six interference fringe images taken while changing the imaging distance is described, the phase restoration may be performed by using four or more differential coefficients obtained from seven or more interference fringe images. Alternatively, with respect to expression (11), the phase restoration may be performed on the basis of the vector $\Phi(x,y)$ that is obtained by using the least-squares method as expressed by expression (15).

$$\vec{\Phi} = -\kappa (A^t A)^{-1} A^t \vec{D} \qquad (15)$$

Further, as expressed by the following expression (16), only the required part for obtaining $\nabla^2 \phi(x,y)$ among the components in expression (11) maybe calculated without using the inverse matrix.

$$\nabla^2 \phi = -\kappa \frac{K_1 \frac{\partial I_1}{\partial z} + K_2 \frac{\partial I_2}{\partial z} + K_3 \frac{\partial I_3}{\partial z}}{K_1 I_1 + K_2 I_2 + K_3 I_3} \qquad (16)$$

Where $$K_1 \equiv \frac{\partial I_3}{\partial x} \frac{\partial I_2}{\partial y} - \frac{\partial I_2}{\partial x} \frac{\partial I_3}{\partial y}$$

$$K_2 \equiv \frac{\partial I_1}{\partial x} \frac{\partial I_3}{\partial y} - \frac{\partial I_3}{\partial x} \frac{\partial I_1}{\partial y}$$

$$K_3 \equiv \frac{\partial I_2}{\partial x} \frac{\partial I_1}{\partial y} - \frac{\partial I_1}{\partial x} \frac{\partial I_2}{\partial y}$$

Figure 4:
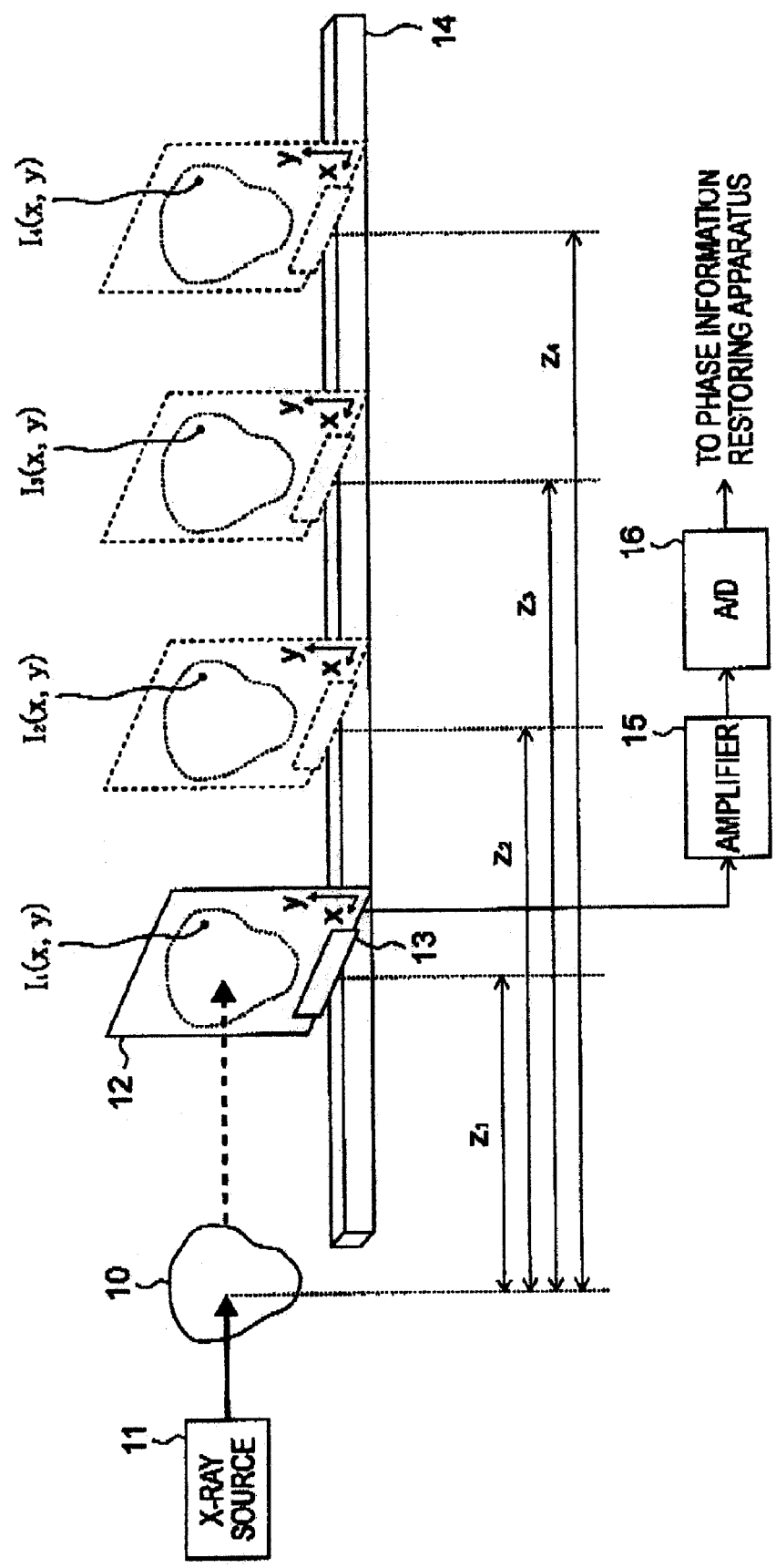
FIG. 4 is an explanatory diagram of a phase information restoring method according to a second embodiment of the present invention.

Next, a phase information restoring method according to a second embodiment of the present invention will be described, referring to FIGS. 1, 3, and 4. FIG. 4 is an explanatory diagram of the phase information restoring method according to the embodiment of the present invention and shows a condition in which X-ray imaging is performed in the imaging unit. In the phase information restoring method according to the embodiment, a visible image is constructed on the basis of image information representing four diffraction fringe images taken with an imaging distance changed.

First, at step S1, X-ray imaging is performed. The sensor 12 is positioned at the position where the imaging distance is $z_1$ and the object 10 is irradiated with an X-ray as shown in FIG. 4 so as to perform the X-ray imaging. Then, the sensor 12 moved to the position where the imaging distance is $z_2$ and the X-ray imaging is similarly performed. Further, the X-ray imaging is repeated with the sensor positioned at the imaging distances of $z_3$ and $z_4$. Thereby, the image information representing diffraction fringe images are obtained.

By the X-ray imaging at step S1, detection data $I_1(x,y)$, $I_2(x,y)$, $I_3(x,y)$, and $I_4(x,y)$ are sequentially input to the phase information restoring apparatus 2 and stored in the storage unit 21. Here, the detection data $I_1(x,y)$ represents intensity of the diffracted X-ray at the position (x,y) on a plane at the imaging distance of $z_1$. The detection data $I_2(x,y)$ to $I_4(x,y)$ similarly represent intensity as above.

Next, at step S2, the differential processing unit 22 obtains a differential coefficient between detection data $I_N$ and detection data $I_{N+1}$ using the following expression (17), where N=1, 2, and 3.

$$\frac{\partial I_N(x,y)}{\partial z} = \frac{I_{N+1}(x,y) - I_N(x,y)}{z_{N+1} - z_N} \qquad (17)$$

The processing at steps S3–S8 are the same as that described in the first embodiment of the present invention.

Although, in the embodiment, phase restoration is performed by using three differential coefficients obtained from four interference fringe images taken while changing the imaging distance, the phase restoration may be performed on the basis of four or more differential coefficients by using five or more interference fringe images.

Figure 5:
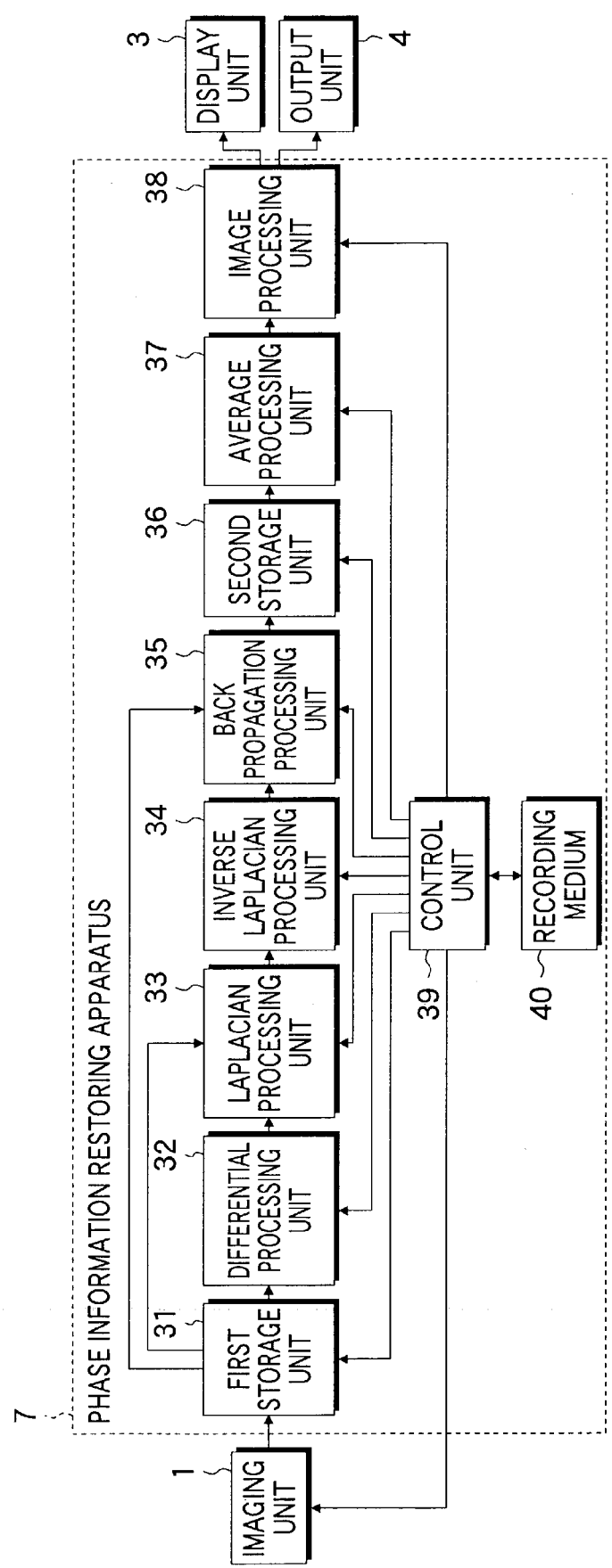
FIG. 5 is a block diagram showing an X-ray imaging system including a phase information restoring apparatus according to a third embodiment of the present invention.

Next, a phase information restoring apparatus according to a third embodiment of the present invention will be described. FIG. 5 is a block diagram showing an X-ray imaging system including the phase information restoring apparatus according to the embodiment of the present invention. This X-ray imaging system has a phase information restoring apparatus 7 for generating image data on the basis of detection data output from the imaging unit 1. Other construction is the same as that of the X-ray imaging system shown in FIG. 1.

The phase information restoring apparatus 7 has a first storage unit 31 for temporarily storing the detection data output from the imaging unit 1, a differential processing unit 32 for obtaining a differential coefficient between detection data at different imaging distances, a Laplacian processing unit 33 for calculating a value corresponding to a Laplacian of phase, an inverse Laplacian processing unit 34 for performing inverse Laplacian operation for phase restoration, a back propagation processing unit 35 for obtaining phase information at a position of an object on the basis of the restored phase information, detection data, and an imaging distance, a second storage unit 36 for temporarily storing the phase information at the position of the object obtained in the back propagation processing unit 35, an average processing unit 37 for averaging plural pieces of phase information at the position of the object, an image processing unit 38 for generating image data based on the averaged phase information, and a control unit 39 for controlling the above respective units 31–38 and the imaging distance in the imaging unit 1. The phase information restoring apparatus 7 may be configured with a digital circuit or software and a CPU. In the latter case, the control unit 39 including the CPU processes the detection data on the basis of a phase information restoration program recorded on a recording medium 40. As the recording medium 40, a flexible disk, a hard disk, an MO, an MT, a RAM, a CD-ROM, a DVD-ROM, etc. are applicable.

Next, a principle of a phase information restoring method according to the present invention will be described. The phase information restoring method according to the present invention is a method of constructing a visible image by the phase-contrast method, and the phase restoration is performed on the basis of plural diffraction fringe images obtained with respect to an object by using the basic expression of phase restoration, TIE (transport of intensity equation).

TIE expressed by the following expression (18) is transformed so as to obtain expression (19).

$$-\kappa \frac{\partial I(x,y)}{\partial z} = \nabla \cdot \{I(x,y) \nabla \phi(x,y)\} \qquad (18)$$

$$-\kappa \frac{\partial I(x,y)}{\partial z} = I(x,y) \nabla^2 \phi(x,y) + \nabla I(x,y) \cdot \nabla \phi(x,y) \qquad (19)$$

Where I(x,y) is detection data representing intensity of diffracted X-ray at a position (x,y) on a plane at a distance of z from the object.

In expression (19), approximating the second term $\nabla I(x,y) \cdot \nabla \phi(x,y)$ included in the right side to zero, the TIE approximation expression (20) is obtained.

$$\frac{\partial I(x,y)}{\partial z} \cong -\frac{I(x,y)}{\kappa}\nabla^2 \phi(x,y) \qquad (20)$$

The phase information restoring apparatus according to the embodiment is for obtaining the phase used for generating image data by restoring plural phases using the above TIE approximation expression (20) and averaging the restored phases.

Figure 6:
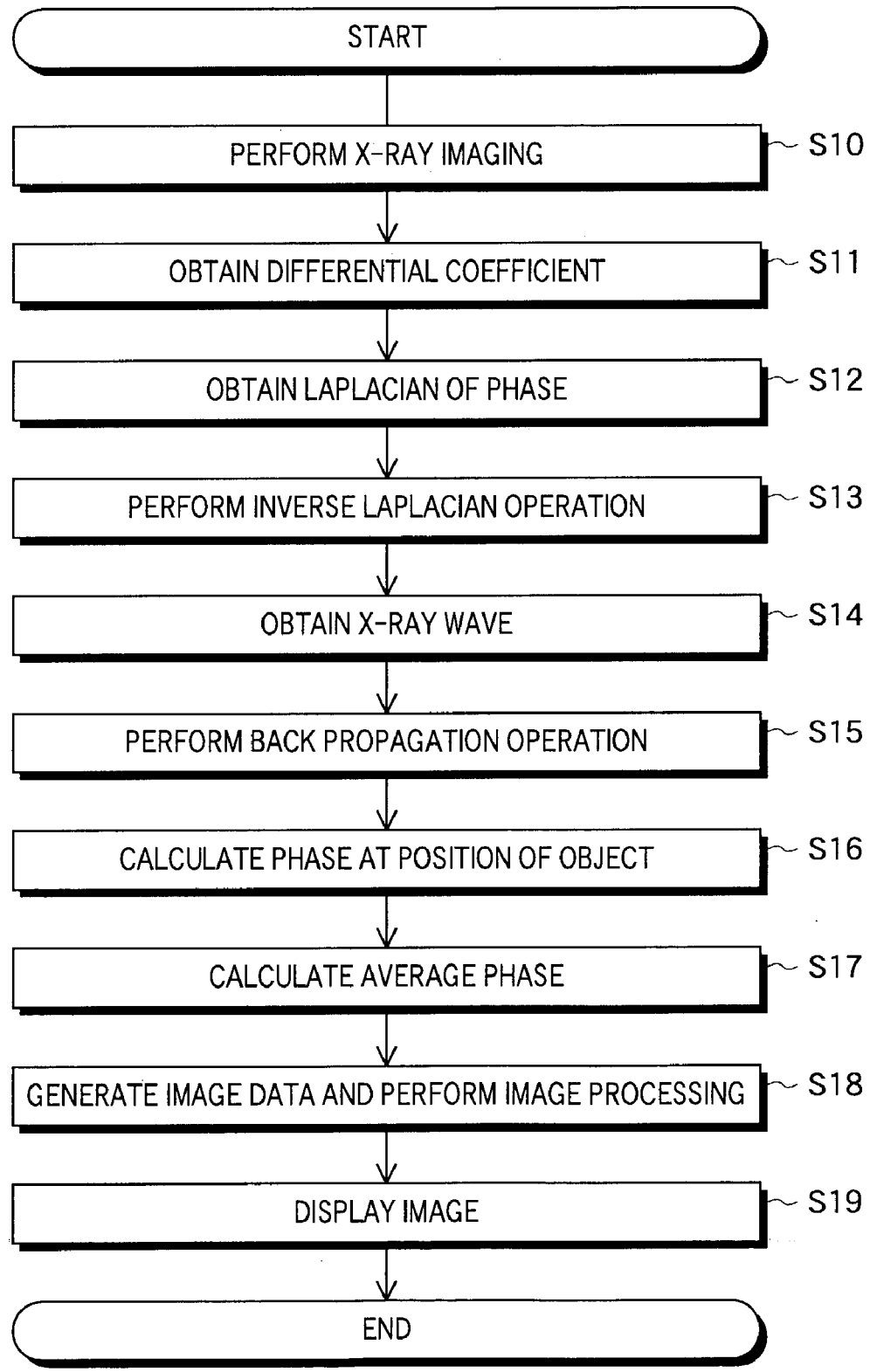
FIG. 6 is a flowchart showing a phase information restoring method according to the third embodiment of the present invention.

Next, referring to FIGS. 2, 5, and 6, the phase information restoring method according to the third embodiment of the present invention will be described. FIG. 6 is a flowchart showing the phase information restoring method according to the third embodiment of the present invention. In the embodiment, a visible image is constructed by using detection data representing six diffraction fringe images taken while changing the imaging distance as shown in FIG. 2.

First, at step S10, X-ray imaging is performed. The sensor 12 is positioned at the position where the imaging distance is $z_1$ and the object 10 is irradiated with an X-ray so as to perform the X-ray imaging. Then, the sensor 12 moved to the position where the imaging distance is $(z_1+\Delta z_1)$ and the X-ray imaging is performed. Similarly, the X-ray imaging is repeated with the sensor 12 positioned at the imaging distances of $z_2$, $(z_2+\Delta z_2)$, $z_3$, and $(z_3+\Delta z_3)$. Thereby, the detection data representing diffraction fringe images are obtained.

By the X-ray imaging at step 510, the detection data $I_1(x,y)$, $I_1'(x,y)$, $I_2(x,y)$, $I_2'(x,y)$, $I_3(x,y)$, and $I_3'(x,y)$ are sequentially input to the phase information restoring apparatus 7. Here, the detection data $I_1(x,y)$ represents intensity of the diffracted X-ray at the position $(x,y)$ on a plane at the imaging distance of $z_1$. Similarly, the detection data $I_1'(x,y)$, $I_2(x,y)$, $I_2'(x,y)$, $I_3(x,y)$, and $I_3'(x,y)$ represent intensity of the diffracted X-ray at the positions $(x,y)$ on planes at the imaging distances of $(z_1+\Delta z_1)$, $z_2$, $(z_2+\Delta z_2)$, $z_3$, $_{and\ (z3}+\Delta z_3)$, respectively. The detection data are sequentially stored in the first storage unit 31 of the phase information restoring apparatus 7.

Next, at steps S11–S13, the phase information restoring apparatus 7 restores a phase at the position of the sensor on the basis of the detection data stored in the first storage unit 31.

First, at step S11, the differential processing unit 32 obtains a differential coefficient between detection data $I_N$ and detection data $I_N'$ using the following expression (21), where $\Delta z_N = z_N' - z_N$ and N=1, 2, and 3.

$$\frac{\partial I_N(x,y)}{\partial z} = \frac{I_N'(x,y) - I_N(x,y)}{\Delta z_N} \qquad (21)$$

Then, at step S12, the Laplacian processing unit 33 obtains Laplacian $f(x,y)=\nabla^2\phi(x,y)$ of a phase on the basis of the differential coefficient obtained at step S11 and the detection data stored in the first storage unit 31, using the following expression (22).

$$f(x,y) = -\frac{\kappa}{I_N(x,y)} \frac{\partial I(x,y)}{\partial z} \qquad (22)$$

Here, in expression (22), although the differential coefficient is divided by the detection data $I_N(x,y)$ at a shorter imaging distance, it may be divided by the detection data $I_N'(x,y)$ at a longer imaging distance or by different detection data from that used when obtaining the differential coefficient. Alternatively, the differential coefficient may be divided by detection data performed with LPF (low pass filter) processing.

Further, at step S13, the inverse Laplacian processing unit 34 performs inverse Laplacian operation on the Laplacian $f(x,y)=\nabla^2\phi(x,y)$ of the phase obtained at step S12 so as to obtain phase $\phi(x,y)$. Note that the inverse Laplacian operation in the inverse Laplacian processing unit 34 is the same as that described using FIG. 3 in the first embodiment of the present invention.

Next, at steps S14–S16, the back propagation processing unit 35 restores a phase of the X-ray just after transmitted through the object on the basis of the restored phase, the detection data $I_1$, $I_2$, and $I_3$ stored in the storage unit 31, and the imaging distances $z_1$, $z_2$, and $z_3$. Hereinafter, a phase etc. of an X-ray just after transmitted through an object is referred to as a phase etc. at the position of the object in relation to a phase etc. of the X-ray at the imaging distance of $z_N$.

First, at step S14, the back propagation processing unit 35 obtains X-ray wave $\psi_N(x,y)$ at the imaging distance of $z_N$ on the basis of the phase $\Phi_N(x,y)$ restored at step S13 and the detection data $I_N(x,y)$ stored in the first storage unit 31, using the following expression (23).

$$\psi_N(x,y) = \sqrt{I_N(x,y)}\ \exp[i\phi_N(x,y)] \qquad (23)$$

Where "i" denotes imaginary unit.

Next, at step S15, the back propagation processing unit 35 obtains X-ray wave $\psi_{N\to 0}(x,y)$ at the position of the object on the basis of the X-ray wave $\psi_N(x,y)$ obtained at step S14 using the following expression (24).

$$\psi_{N\to 0}(x,y) = h_{-zN}(x,y) * \psi_N(x,y) \qquad (24)$$

Where "*" denotes convolution and $$h_z(x,y) = \frac{1}{i\lambda z} e^{\frac{i\pi}{\lambda z}(x^2+y^2)}$$

Further, at step S16, the back propagation processing unit 35 calculates phase $\phi_{N\to 0}(x,y)$ at the position of the object on the basis of the X-ray wave $\psi_{N\to 0}(x,y)$ at the position of the object obtained at step S15, using the following expression (25). The calculated phase $\phi_{N\to 0}(x,y)$ is sequentially stored in the second storage unit 36.

$$\phi_{N\to 0}(x,y) = \tan^{-1}\left[\frac{\mathrm{Im}[\Psi_{N\to 0}(x,y)]}{\mathrm{Re}[\Psi_{N\to 0}(x,y)]}\right] \qquad (25)$$

Where Re [ ] and Im [ ] are functions for obtaining the real part and the imaginary part, respectively.

Next, at step S17, the average processing unit 37 calculates average phase $\phi_0(x,y)$ at the position of the object on the basis of the phase $\phi_0(x,y)$ at the position of the object stored in the second storage unit 36 using the following expression (26).

$$\phi_0(x,y) = \frac{1}{3} \sum_{N=1,2,3} \phi_{N\to 0}(x,y) \quad (26)$$

Then, at step S18, the image processing unit 38 generates image data on the basis of the average phase $\phi_0(x,y)$. That is, the image processing unit 38 converts the average phase $\phi_0(x,y)$ in each pixel into data representing brightness and performs necessary image processing such as gradation processing and interpolation processing.

At step S19, the display unit 3 and the output unit 4 displays a visible image on a screen or a film on the basis of the image data generated as described above.

Although, in the embodiment, the method of restoring phase by using three differential coefficients obtained from six interference fringe images taken while changing the imaging distance is described, the phase restoration may be performed on the basis of two differential coefficients, or the images used when obtaining different differential coefficients may be duplicated.

Figure 7:
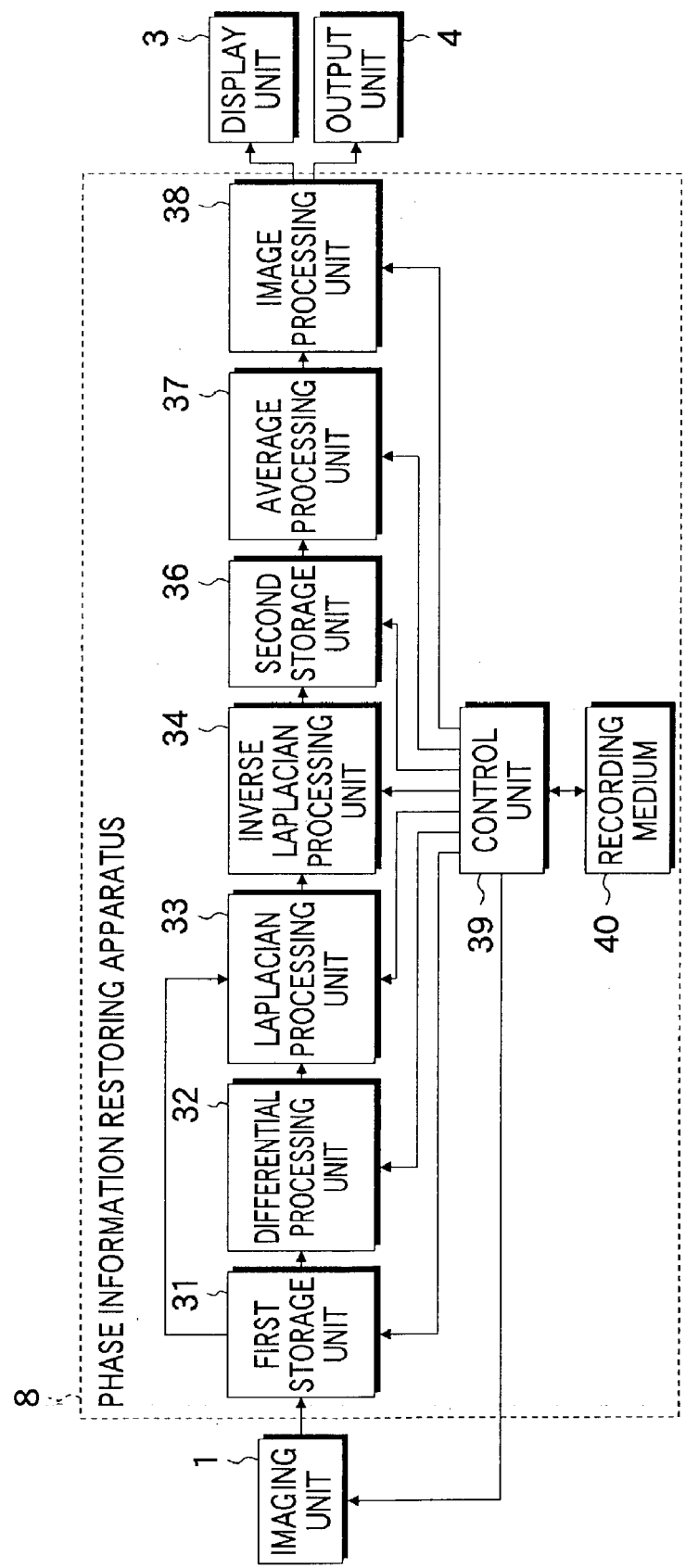
FIG. 7 is a block diagram showing an X-ray imaging system including a phase information restoring apparatus according to a fourth embodiment of the present invention.

Next, a phase information restoring apparatus according to a fourth embodiment of the present invention will be described. FIG. 7 is a block diagram showing an X-ray imaging system including the phase information restoring apparatus according to the fourth embodiment of the present invention. This X-ray imaging system includes a phase information restoring apparatus 8 instead of the phase information restoring apparatus 7 in FIG. 5. Other construction is the same as that in FIG. 5.

The phase information restoring apparatus 8 has a first storage unit 31 for temporarily storing the detection data output from the imaging unit 1, a differential processing unit 32 for obtaining a differential coefficient between detection data at different imaging distances, a Laplacian processing unit 33 for calculating a value corresponding to a Laplacian of phase, an inverse Laplacian processing unit 34 for performing an inverse Laplacian operation for performing phase restoration, a second storage unit 36 for temporarily storing the phase information at the position of the sensor output from the inverse Laplacian processing unit 34, an average processing unit 37 for averaging plural pieces of phase information, an image processing unit 38 for generating image data based on the averaged phase information, and a control unit 39 for controlling the above respective units 31–38 and the imaging distance in the imaging unit 1. The phase information restoring apparatus 8 may be configured with a digital circuit or software and a CPU.

Figure 8:
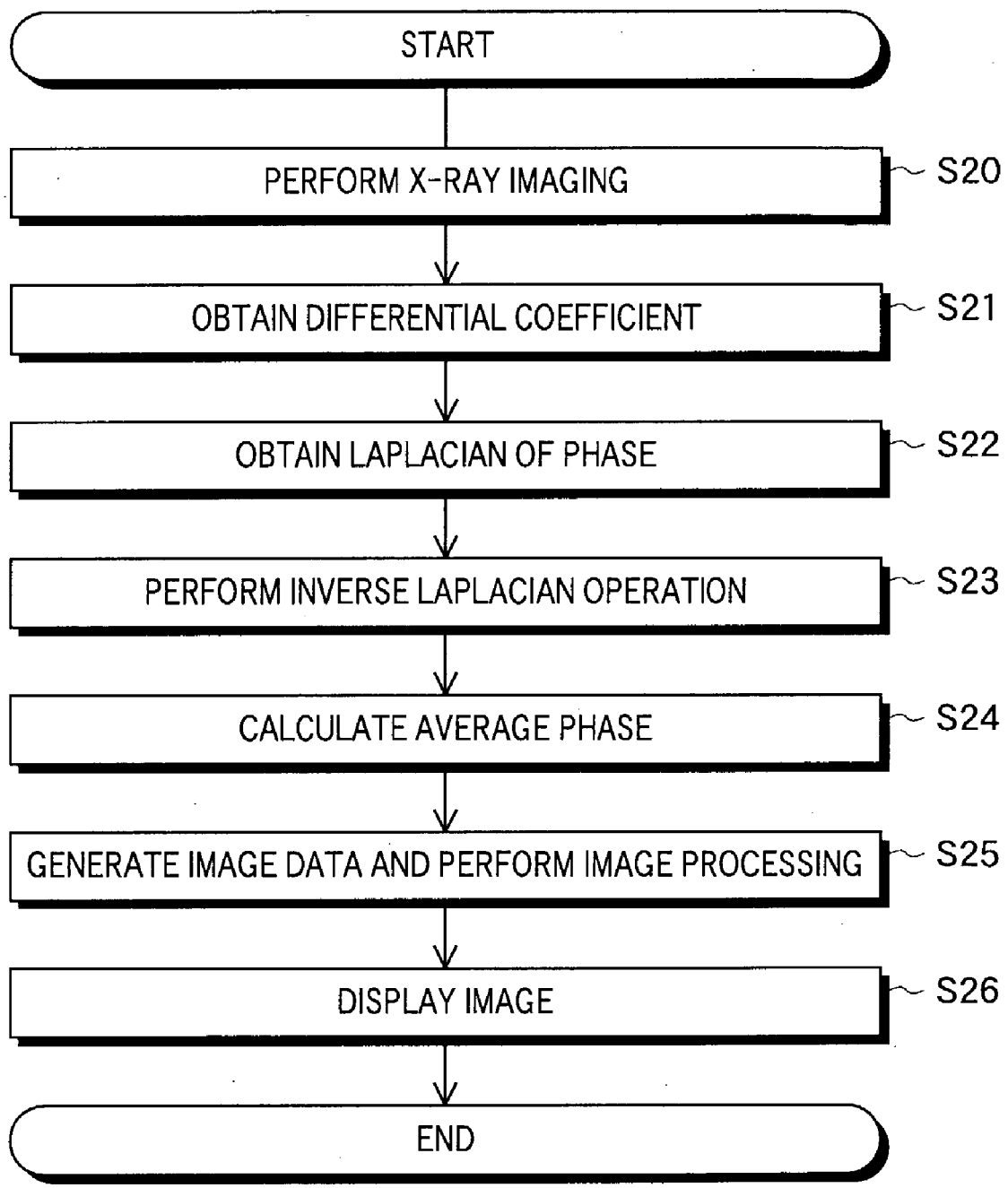
FIG. 8 is a flowchart showing a phase information restoring method according to the fourth embodiment of the present invention.

Next, a phase information restoring method according to the fourth embodiment of the present invention will be described, referring to FIGS. 2, 7, and 8. FIG. 8 is a flowchart showing the phase information restoring method according to the fourth embodiment of the present invention. In the embodiment, a visible image is constructed by using image information representing six diffraction fringe images taken while changing the imaging distance. The method is characterized by using TIE approximation expression expressed by expression (20) and performing appropriate approximation when constructing an operation expression so as to perform operation easily and speedy.

First, at step S20, X-ray imaging is performed. The sensor 12 is positioned at the position where the imaging distance is $z_1$ and the object 10 is irradiated with an X-ray as shown in FIG. 2 so as to perform the X-ray imaging. Subsequently, the sensor 12 moved to the position where the imaging distance is $(z_1+\Delta z_1)$ and the X-ray imaging is similarly performed. Further, the X-ray imaging is repeated with the sensor 12 positioned at the imaging distances of $z_2$, $(z_2+\Delta z_2)$, $z_3$, and $(z_3+\Delta z_3)$. Thereby, the image information representing diffraction fringe images are obtained.

By the X-ray imaging at step S20, the detection data $I_1(x,y)$, $I_1'(x,y)$, $I_2(x,y)$, $I_2'(x,y)$, $I_3(x,y)$, and $I_3'(x,y)$ are sequentially input to the phase information restoring apparatus 8. Here, the detection data $I_1(x,y)$ represents intensity of the diffracted X-ray at the position (x,y) on a plane at the imaging distance of $z_1$. Similarly, the detection data $I_1'(x,y)$, $I_2(x,y)$, $I_2'(x,y)$, $I_3(x,y)$, and $I_3'(x,y)$ represent intensity of the diffracted X-ray at the positions (x,y) on planes at the imaging distances of $(z_1+\Delta z_1)$, $z_2$, $(z_2+\Delta z_2)$, $z_3$, and $(z_3+\Delta z_3)$, respectively. The detection data are sequentially stored in the first storage unit 31 of the phase information restoring apparatus 8.

Next, at steps S21–S23, the phase information restoring apparatus 8 restores a phase at the position of the sensor on the basis of the detection data stored in the first storage unit 31.

First, at step S21, the differential processing unit 32 obtains a differential coefficient between detection data $I_N$ and detection data $I_N'$.

Then, at step S22, the Laplacian processing unit 33 obtains Laplacian $f(x,y)=\nabla^2\phi(x,y)$ of a phase on the basis of the differential coefficient obtained at step S21 and the detection data stored in the first storage unit 31.

Further, at step S23, the inverse Laplacian processing unit 34 performs an inverse Laplacian operation on the Laplacian $f(x,y)=\nabla^2\phi(x,y)$ of the phase obtained at step S22 so as to calculate phase $\phi(x,y)$. The calculated phase $\phi(x,y)$ is sequentially stored in the second storage unit 36.

Next, at step S24, the average processing unit 37 calculates average phase $\phi_0(x,y)$ based on the phase $\phi_N(x,y)$ at the position of the sensor stored in the second storage unit 36.

Further, at step S25, the image processing unit 38 generates image data based on the average phase $\phi_0(x,y)$. That is, the image processing unit 38 converts the average phase $\phi_0(x,y)$ in each pixel into data representing brightness and performs necessary image processing such as gradation processing and interpolation processing.

At step S26, the display unit 3 and the output unit 4 display a visible image on a screen or a film on the basis of the image data generated as described above.

In the embodiment, the phases $\phi_1$ to $\phi_3$ at different imaging distances are averaged as at step 524. In the strict sense, these phases $\phi_1$ to $\phi_3$ include differences in accordance with the changes in the imaging distances in relation to the phase $\phi_0$ at the position of the object. However, when a radiation source such as a synchrotron radiation source that generates a highly directional beam is used, these phases $\phi_1$, $\phi_2$, and $\phi_3$ can be approximated equal to the phase $\phi_0$ at the position of the object. Further, averaging the phases $\phi_1$ to $\phi_3$ can cancel errors and bring the averaged phase closer to the real phase $\phi_0$.

Although, in the first to fourth embodiments of the present invention described above, X-rays are used when imaging is performed on an object, any beam other than X-rays that can be transmitted through the object and form diffraction images, such as particle beams including an electron beam, may be used.

Further, in the first to fourth embodiments of the present invention, although a synchrotron radiation source is used when imaging is performed on an object, a radiation source generating beams other than synchrotron radiation may be used. For example, an electron storage type high brightness hard X-ray generator, which has been developed by Ritsumeikan University, can generate X-rays having as high brightness and directivity as synchrotron radiation despite of its tabletop size. X-rays generated by this generator have coherency, and even though the X-rays have plural wavelengths, they can be monochromatized by combining with monochromatizing crystal. Furthermore, the radiation source developed by The Femtosecond Technology Research Association (FESTA) generates ultrashort pulse high-brightness X-rays based on a principle of backward Compton scattering. This ray source is compact and portable, and can generate X-rays having not only coherency but also high directivity and monochromaticity. Note that, if a point source of radiation is used as a radiation source, it is desirable to correct the detection data to include magnification when performing data processing in the phase information restoring apparatus.

Next, a modified example of the X-ray imaging system including the phase information restoring apparatus according to the first to fourth embodiments of the present invention will be described. The X-ray imaging system shown in FIG. 9 has a reading unit 5 and an imaging unit 6 instead of the imaging unit 1 in the X-ray imaging system shown in FIG. 1. Other construction is the same as that of the X-ray imaging system shown in FIG. 1.

In the imaging unit 6, as a screen used for recording image information, a photostimulable phosphor sheet (recording sheet) is used instead of the sensor 12 in the imaging unit 1 shown in FIG. 2.

The photostimulable phosphor (storage phosphor) is a material that, when applied with radiation, a part of the radiation energy is stored therein, and when applied with excitation light such as visible light afterward, light is photostimulably emitted in accordance with the stored energy. When a radiation image of an object such as a human body is taken and recorded on the sheet applied with the photostimulable phosphor, and scanned by the excitation light such as laser light, stimulated fluorescent light is generated. Therefore, detection data can be obtained by reading the light photoelectrically. After the detection data is appropriately processed, the radiation image can be displayed as a visible image by outputting to a display such as a CRT or printing out on a film by a laser printer etc.

Figure 9:
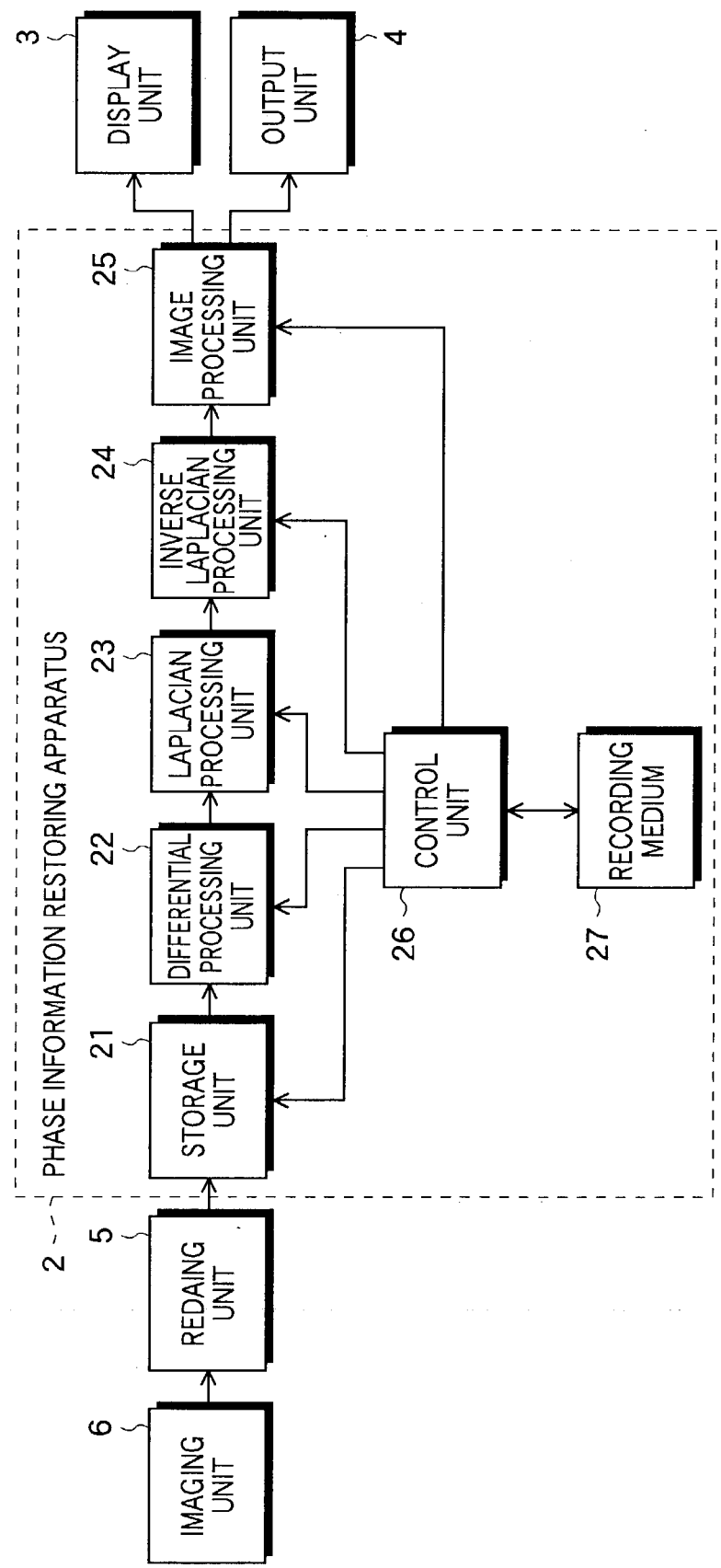
FIG. 9 is a block diagram showing a modified example of the X-ray imaging system shown in FIG. 1.
Figure 10:
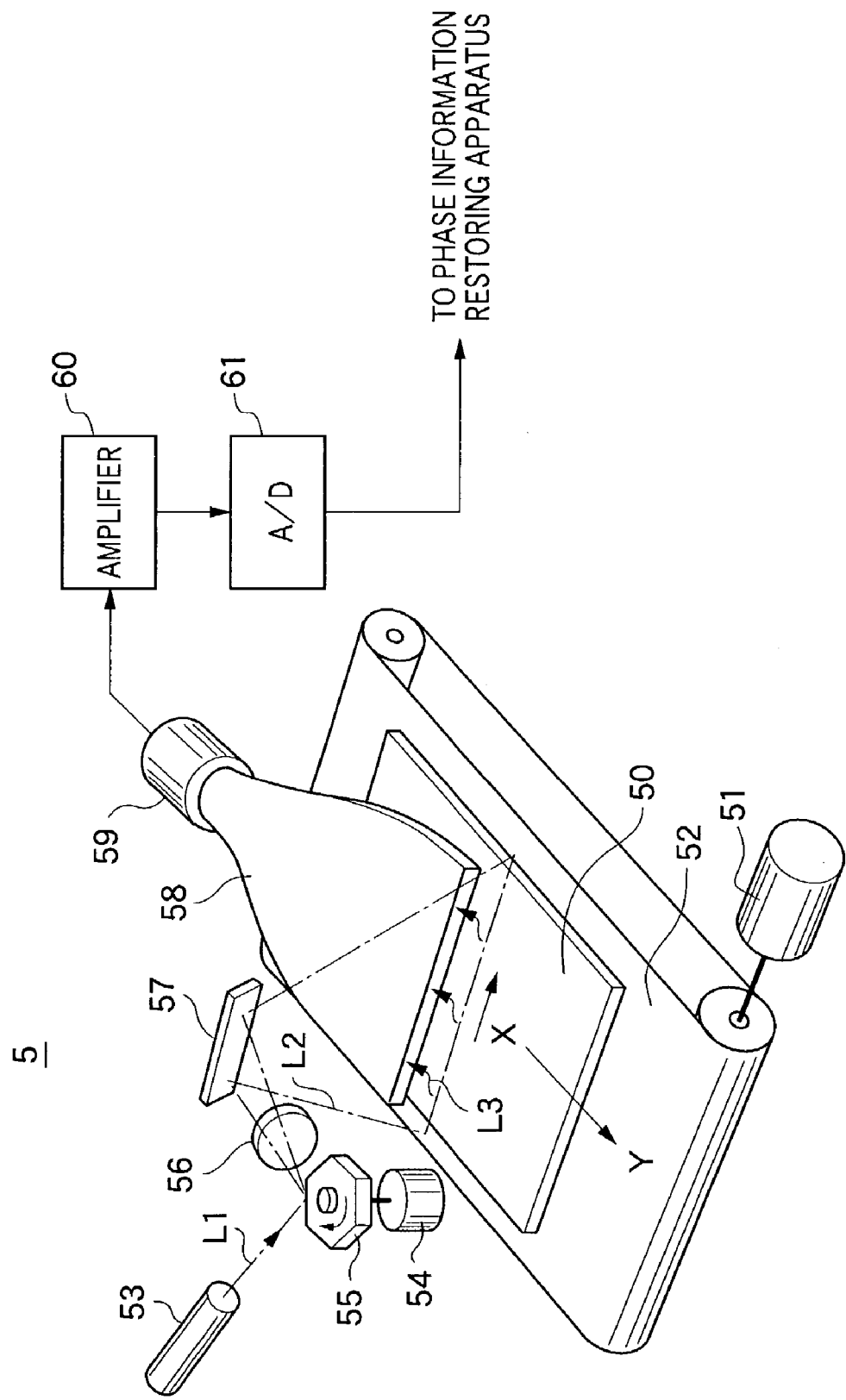
FIG. 10 is a diagram showing a structure of a reading unit shown in FIG. 9.
Figure 11:
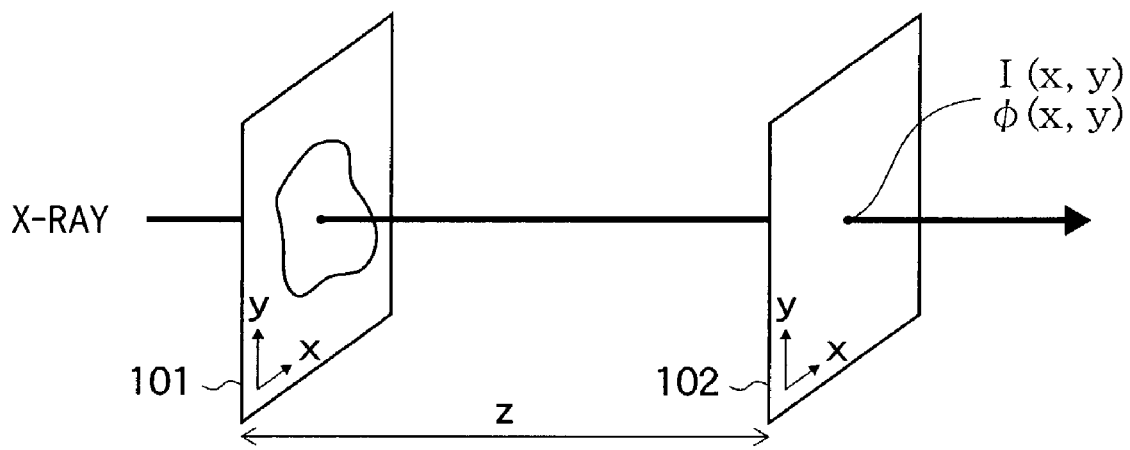
FIG. 11 is an explanatory diagram showing a principle of phase restoration.

The reading unit 5 shown in FIG. 9 is used for reading the radiation image recorded on the recording sheet. Here, referring to FIG. 10, construction and operation of the reading unit 5 will be described. The recording sheet 50 on which image information has been recorded is set in a predetermined position in the reading unit 5. The recording sheet 50 is carried in Y-direction by a sheet carrying means 52 driven by a motor 51. On the other hand, a beam L1 oscillating from the laser source 53 is reflected and deflected by a rotating polygon mirror 55 driven by a motor 54 and rotating at high speed in a direction of an arrow, and passes through a convergent lens 56. Then, the beam L1 changes its optical path by the mirror 57 and scans the recording sheet 50 in X-direction. By the scanning, excitation light L2 is applied to the recording sheet 50, and stimulated fluorescent light L3 having intensity in accordance with the stored and recorded radiation image information is emitted from the applied part. The stimulated fluorescent light L3 is guided by the optical guide 58 and photoelectrically detected by a photomultiplier 59. An analogue signal output from the photomultiplier 59 is amplified by an amplifier 60 and digitized by an A/D converter 61. The detection data output from the A/D converter 61 is input to the phase information restoring apparatus 2.

Image information representing plural interference fringe images obtained at different imaging distances can be obtained by performing radiation imaging with the imaging distance changed and using plural recording sheets in the imaging unit 6, and reading image information from the respective recording sheets in the reading unit 5. The phase information restoring apparatus 2 performs phase restoration based on the image information and generates image data. The processing in the phase information restoring apparatus 2 is the same as that described using FIG. 3.

The X-ray imaging system shown in FIGS. 5 and 7 can also be modified into an X-ray imaging system using a photostimulable phosphor sheet similarly to that shown in FIG. 9.

As described above, according to the present invention, a high-accuracy phase restoration can be easily performed by minimizing approximation in TIE and performing operation using matrices. Thus, a visible image of good quality can be obtained by the phase-contrast method.

Further, according to the present invention, phase information of high accuracy can be obtained by averaging the plural restored phases to obtain the phase used as image data. Therefore, a visible image of good quality in which noise is cancelled can be obtained by using the above phase information.

The invention claimed is:

1. A phase information restoring method of restoring phase information of radiation transmitted through an object on the basis of an image signal obtained by detecting intensity of the radiation transmitted through the object, said method comprising the steps of:

(a) obtaining at least three first differential signals representing differentials between one image signal and another image signal on the basis of at least four image signals obtained by detecting intensity of radiation on at least four planes that are parallel and positioned at different distances from the object, said at least four image signals respectively representing radiation image information on said at least four planes;

(b) obtaining second differential signals and third differential signals representing differentials between image signals relative to two directions orthogonal to each other within said planes with respect to at least three image signals;

(c) obtaining a Laplacian of phase on the basis of the at least three image signals and at least three sets of the first to third differential signals; and (d) performing inverse Laplacian operation on the Laplacian of phase so as to restore phase information.

2. A phase information restoring method according to claim 1, wherein step (c) includes obtaining the Laplacian of phase by using an inverse matrix of a matrix having elements of the at least three image signals and at least three sets of the second and third differential signals.

3. A phase information restoring method of restoring phase information of radiation transmitted through an object on the basis of an image signal obtained by detecting intensity of the radiation transmitted through the object, said method comprising the steps of:

(a) obtaining plural differential signals representing differentials between one image signal and another image signal on the basis of at least three image signals obtained by detecting intensity of radiation on at least three planes that are positioned at different distances from the object, said at least three image signals respectively representing radiation image information on said at least three planes;

(b) respectively obtaining Laplacian of phases on the basis of said plural differential signals and one of said at least three image signals;

(c) performing inverse Laplacian operation on the Laplacian of phases so as to obtain plural phases respectively;

(d) calculating an average value of the plural phases obtained at step (c).

4. A phase information restoring method according to claim 3, wherein step (c) includes respectively calculating waves of the radiation on the planes on the basis of the image signals used when obtaining the respective differential signals at step (a) and the plural phases restored by using the respective differential signals, converting the waves of the radiation on said planes into plural waves on a predetermined plane by back propagation calculation, and obtaining plural phases on said predetermined plane.

5. A phase information restoring apparatus for restoring phase information of radiation transmitted through an object on the basis of an image signal obtained by detecting intensity of the radiation transmitted through the object, said apparatus comprising:

differential processing means for obtaining at least three first differential signals representing differentials between one image signal and another image signal on the basis of at least four image signals obtained by detecting intensity of radiation on at least four planes that are parallel and positioned at different distances from the object, said at least four image signals respectively representing radiation image information on said at least four planes, and obtaining second differential signals and third differential signals representing differentials between image signals relative to two directions orthogonal to each other within said planes with respect to at least three image signals;

Laplacian processing means for obtaining a Laplacian of phase on the basis of the at least three image signals and at least three sets of the first to third differential signals;

inverse Laplacian processing means for performing inverse Laplacian operation on the Laplacian of phase so as to restore phase information.

6. A phase information restoring apparatus according to claim 5, wherein said Laplacian processing means obtains the Laplacian of phase by using an inverse matrix of a matrix having elements of the at least three image signals and at least three sets of the second and third differential signals.

7. A phase information restoring apparatus for restoring phase information of radiation transmitted through an object on the basis of an image signal obtained by detecting intensity of the radiation transmitted through the object, said apparatus comprising:

differential processing means for obtaining plural differential signals representing differentials between one image signal and another image signal on the basis of at least three image signals obtained by detecting intensity of radiation on at least three planes that are positioned at different distances from the object, said at least three image signals respectively representing radiation image information on said at least three planes;

Laplacian processing means for respectively obtaining Laplacian of phases based on said plural differential signals and one of said at least three image signals;

inverse Laplacian processing means for performing inverse Laplacian operation on the Laplacian of phases so as to obtain plural phases respectively;

average processing means for calculating an average value of the plural phases obtained in said inverse Laplacian processing means.

8. A phase information restoring apparatus according to claim 7, wherein said inverse Laplacian processing means respectively calculates waves of the radiation on the planes on the basis of the image signals used when obtaining the respective differential signals in said differential processing means and the plural phases restored by using the respective differential signals, converts the waves of the radiation on said planes into plural waves on a predetermined plane by back propagation calculation, and obtains plural phases on said predetermined plane.

9. A phase information restoring program, embodied on a computer readable medium, to be used for restoring phase information of radiation transmitted through an object on the basis of an image signal obtained by detecting intensity of the radiation transmitted through the object, said program allowing a CPU to execute the procedures of:

obtaining at least three first differential signals representing differentials between one image signal and another image signal on the basis of at least four image signals obtained by detecting intensity of radiation on at least four planes that are parallel and positioned at different distances from the object, said at least four image signals respectively representing radiation image information on said at least four planes;

obtaining second differential signals and third differential signals representing differentials between image signals relative to two directions orthogonal to each other within said planes with respect to at least three image signals;

obtaining a Laplacian of phase on the basis of the at least three image signals and at least three sets of the first to third differential signals; and performing inverse Laplacian operation on the Laplacian of phase so as to restore phase information.

10. A phase information restoring program. embodied on a computer readable medium, to be used for restoring phase information of radiation transmitted through an object on the basis of an image signal obtained by detecting intensity of the radiation transmitted through the object, said program allowing a CPU to execute the procedures of:

(a) obtaining plural differential signals representing differentials between one image signal and another image signal on the basis of at least three image signals obtained by detecting intensity of radiation on at least three planes that are positioned at different distances from the object, said at least three image signals respectively representing radiation image information on said at least three planes;

(b) respectively obtaining Laplacian of phases on the basis of said plural differential signals and one of said at least three image signals;

(c) performing inverse Laplacian operation on the Laplacian of phases so as to obtain plural phases respectively;

(d) calculating an average value of the plural phases obtained in procedure (c).

* * * * *